US012324892B2

(12) United States Patent
Niederauer et al.

(10) Patent No.: US 12,324,892 B2
(45) Date of Patent: Jun. 10, 2025

(54) WOUND OXYGEN TREATMENT SYSTEM

(71) Applicant: ELECTROCHEMICAL OXYGEN CONCEPTS, INC., San Antonio, TX (US)

(72) Inventors: Mark Q Niederauer, San Antonio, TX (US); James P. Daley, San Antonio, TX (US); Joseph J. Moffett, Crownsville, MD (US)

(73) Assignee: Electrochemical Oxygen Concepts, Inc., San Antonio, TX (US)

( * ) Notice: Subject to any disclaimer, the term of this patent is extended or adjusted under 35 U.S.C. 154(b) by 910 days.

(21) Appl. No.: 17/603,631

(22) PCT Filed: Apr. 15, 2020

(86) PCT No.: PCT/US2020/028312
§ 371 (c)(1),
(2) Date: Oct. 14, 2021

(87) PCT Pub. No.: WO2020/214698
PCT Pub. Date: Oct. 22, 2020

(65) Prior Publication Data
US 2022/0193326 A1    Jun. 23, 2022

Related U.S. Application Data

(60) Provisional application No. 62/833,878, filed on Apr. 15, 2019.

(51) Int. Cl.
*A61M 35/00* (2006.01)
*A61M 1/00* (2006.01)

(52) U.S. Cl.
CPC ............. *A61M 35/30* (2019.05); *A61M 1/74* (2021.05); *A61M 1/75* (2021.05); *A61M 1/85* (2021.05);
(Continued)

(58) Field of Classification Search
CPC .......... A61M 35/30; A61M 1/74; A61M 1/75; A61M 1/85; A61M 1/91; A61M 1/94;
(Continued)

(56) References Cited

U.S. PATENT DOCUMENTS 8,287,506 B2 * 10/2012 Wells ................... A61M 35/003
604/23
9,730,838 B2 * 8/2017 Wells ..................... A61M 35/00
(Continued)

FOREIGN PATENT DOCUMENTS

EP          2066365 A1    6/2009
JP       2018-536528 T   12/2018
(Continued)

OTHER PUBLICATIONS

International Search Report and Written Opinion dated Jul. 2, 2020 issued in PCT App. No. PCT/US2020/028312 (14 pages).
(Continued)

*Primary Examiner* — Jessica Arble
(74) *Attorney, Agent, or Firm* — Haynes and Boone, LLP; William B. Nash; Brooke Parker

(57) ABSTRACT

A wound treatment system includes a processor coupled to sensor system(s), a power delivery system, an oxygen concentrator coupled to the power delivery system and including an oxygen outlet coupled to a restricted airflow enclosure provided by a dressing and located adjacent a wound site, and a negative pressure system that includes a negative pressure outlet coupled to the restricted airflow enclosure. The processor receives first sensor information from the sensor system(s), and uses the first sensor information to control the power provided from the power delivery system to the oxygen concentrator in order to control an oxygen flow created by the oxygen concentrator and provided through the oxygen outlet to the restricted airflow enclosure.
(Continued)

When the processor receives second sensor information from the sensor system(s), it activates the negative pressure system to create a fluid flow from the restricted airflow enclosure and through the negative pressure outlet.

9 Claims, 6 Drawing Sheets

(52) U.S. Cl.
CPC .............. *A61M 1/91* (2021.05); *A61M 1/94* (2021.05); *A61M 1/966* (2021.05); *A61M 1/96* (2021.05); *A61M 2202/0208* (2013.01); *A61M 2205/13* (2013.01); *A61M 2205/15* (2013.01); *A61M 2205/18* (2013.01); *A61M 2205/3334* (2013.01)

(58) Field of Classification Search
CPC .............. A61M 1/966; A61M 1/96; A61M 2202/0208; A61M 2205/3334
See application file for complete search history.

(56) References Cited

U.S. PATENT DOCUMENTS

| | | | |
|---|---|---|---|
| 10,226,610 B2* | 3/2019 | Wells | A61M 35/30 |
| 10,702,686 B2 | 7/2020 | Niederauer et al. | |
| 2007/0118096 A1 | 5/2007 | Smith et al. | |
| 2015/0290364 A1* | 10/2015 | Wall | A61M 35/30 604/23 |
| 2017/0165405 A1 | 6/2017 | Muser et al. | |
| 2019/0001107 A1 | 1/2019 | Niederauer et al. | |

FOREIGN PATENT DOCUMENTS

| | | |
|---|---|---|
| WO | WO 2008/039314 A2 | 4/2008 |
| WO | WO 2018/227144 A | 12/2018 |
| WO | WO 2018/227144 A1 | 12/2018 |
| WO | WO 2019/005573 A | 1/2019 |

OTHER PUBLICATIONS

Chinese office action dated Oct. 27, 2022 issued in Chinese patent application No. 202080033011.3 with English translation (12 pages).
European Supplementary Search Report dated Dec. 9, 2022 issued in European patent application No. 20792109.9 (9 pages).
Office Action dated Feb. 28, 2024 issued in related Japanese App. No. 2021-561759 (10 pages with translation).

* cited by examiner

WOUND OXYGEN TREATMENT SYSTEM

RELATED APPLICATIONS

The present disclosure claims the benefit of and priority to U.S. Provisional Patent Application 62/833,878, filed Apr. 15, 2019, and PCT Patent Application No. PCT/US2020/028312, filed Apr. 15, 2020, both entitled "Wound Oxygen Treatment System," which are hereby incorporated by reference in their entirety.

BACKGROUND

The present disclosure relates generally to wound healing via the supply of oxygen to a wound to accelerate the healing of damaged tissue and/or promote tissue viability, and more particularly to the use of intermittent vacuum/suction of a wound site enclosure adjacent a wound site to optimize oxygen concentration adjacent the wound while removing exudate and other fluids from adjacent the wound site.

When tissue is damaged and a wound results, a four phase healing process begins, and optimal metabolic function of cells in the tissue to repopulate the wound requires that oxygen be available for all of these phases of wound healing. Furthermore, the more layers of tissue that are damaged, the greater the risk is for complications to occur in the wound healing process, and difficult-to-heal wounds can encounter barriers to the wound healing process and experience delays in one or more of the last three phases of wound healing. For example, one of the most common contributing factors to delays in the healing of wounds such as venous leg ulcers, diabetic foot ulcers, and pressure ulcers, is the problem of chronic wound ischemia. Chronic wound ischemia a pathological condition that restricts blood supply, oxygen delivery, and blood request for adequate oxygenation of tissue, which inhibits normal wound healing.

One conventional standard of care for treating difficult-to-heal wounds involves the use of an advanced wound dressing, or a combination of advanced wound dressings, that provide a dressing treatment system. The advanced wound dressing may be positioned on the wound site and, in some cases, the surrounding intact skin, to provide a wound site enclosure. The advanced wound dressing typically includes materials having properties for promoting moist wound healing, managing wound exudate, and helping control wound bioburden. Those materials provided in combination operate to produce limited moisture vapor permeability, and the more occlusive the dressing, the lower the amount of ambient air (and thus a respective lower amount of oxygen) that is available to the wound site.

100% oxygen exerts a partial pressure of 760 millimeters (mm) of mercury (Hg), and ambient air includes about 21% oxygen, so ambient air exerts a partial pressure of oxygen of about 159 mm Hg. A typical advanced wound dressing or wound dressing system utilizing materials that provide limited moisture vapor permeable operates to impacts the available oxygen for the wound site, thereby limiting the partial pressure of oxygen at the enclosed wounds site to about 10-60 mm Hg. Fresh air (and its associated higher oxygen amount) is then only provided to the wound site when the dressing is changed, and dressings may remain covering the wound site for up to seven days before a dressing change is required. As such, the limited moisture vapor permeability of advanced wound dressings produce a reduced oxygen wound environment that works against the optimal metabolic function of cells to repopulate the wound during all the phases of wound healing.

Specific examples of conventional systems and methods to provide tissue oxygenation for difficult-to-heal wounds include the intermitted or continuous application of topical hyperbaric oxygen to the wound site. Intermittent topical hyperbaric oxygen treatment systems involve providing a sealed extremity or partial body chamber, along with a connected source of pure oxygen at a relatively high flow rate, and positioning the wounded limb or body area in the sealed extremity chamber or partial body chamber. The oxygen source will then supply the chamber with up to 100% oxygen at flow rates that may exceed 300 liters per hour, pressurizing the interior of the chamber at up to 1.05% normal atmospheric pressure, thereby topically increasing the available oxygen for cellular processing at the affected wound site. For example, during oxygen application, the partial pressure of oxygen exerted inside the sealed extremity or partial body chamber may attain 798 mm Hg, and may be applied for about 90 minutes. These and similar methods of applying intermittent topical hyperbaric oxygen are restrictive, cumbersome, can only supply oxygen to the affected area intermittently with no systemic application, and only provide for a minimal increase in atmospheric pressure (about 5%). Therefore, the effects of the oxygen therapy on wounds using these methods tend to be minimal, which is evidenced by the lack of commercial success of topical hyperbaric oxygen extremity chambers.

Other conventional systems and methods to provide tissue oxygenation include disposable devices that provide for the transmission of gases in ionic form through ion-specific membranes in order to apply supplemental oxygen directly to a wound site. These devices are typically battery powered, disposable, oxygen supplemented bandages that are provided directly over the wound site, and utilize electrochemical oxygen generation using variations of a 4 electron formula originally developed for NASA. In such systems, the amount of oxygen that can be applied to the wound is typically in the range of 3 to 15 milliliters per hour, and desired oxygen flow rates are generated by utilizing corresponding, preselected battery sizes with predefined amperages. As such, these devices are either "on or off", and do not have the ability to deliver a varying or adjustable oxygen flow or oxygen flow rate without obtaining a new device and/or a different battery having an amperage that will produce the desired flow rate. The utilization of fixed, non-variable oxygen flows and oxygen flow rates introduces corresponding limitations in the treatment of different sizes and types of wounds, and tends to result in the wound treatment system being oversized or undersized for the wound to which it is being applied.

The inventors of the present disclosure co-invented systems and methods that address the issues with the conventional wound treatment systems discussed above. For example, U.S. Pat. Nos. 8,287,506, 10,226,610, and U.S. Patent Publication No. 2019/0001107 (collectively the "Incorporated References," the disclosures of which are incorporated by reference herein in their entirety) describe wound treatment systems that provide for low flow tissue oxygenation and continuous oxygen adjustability to wound site(s) to create a controlled hyperoxia and hypoxia wound environment for damaged tissue, accelerates wound healing, and promotes tissue viability. Those systems and methods operate by monitoring pressure information that is indicative of a pressure in a restricted airflow enclosure that is located adjacent a wound site (e.g., provided by a wound dressing), monitoring humidity information that is indicative of an ambient humidity, and/or using other using other characteristics to control power provided to an oxygen production subsystem in order to control an oxygen flow that is created by the oxygen production subsystem and provided to the restricted airflow enclosure. In some embodiments, those wound treatment systems include a flow sensor that measures the oxygen output of the oxygen production subsystem, with a pressure sensor downstream of the flow sensor that measures the pressure that may be utilized to control the oxygen flow created by the oxygen production subsystem as discussed above, a humidity sensor that measures the ambient humidity that may be utilized to control the oxygen flow created by the oxygen production subsystem as discussed above, and/or other sensor subsystems for use in controlling the oxygen flow created by the oxygen production subsystem as discussed above.

However, the inventors of the present disclosure have discovered that achieving the oxygen concentrations that provide for enhanced or optimal wound healing can take a relatively long amount of time, as the wound site enclosure created when a wound dressing is applied to a wound often includes a relatively large volume of relatively low-oxygen-concentration air (a volume which increases as the wound dressing is larger in size) that must be replaced by the high concentration oxygen produced by the oxygen production subsystems discussed above. Furthermore, the changing of wound dressings will release the relatively high concentration oxygen that has been provided in the wound site enclosure by the oxygen production subsystems discussed above, and thus each wound dressing change introduces the problem discussed above of "resetting the clock" to build up the relatively high concentration oxygen in the wound site enclosure and adjacent the wound site that provides the benefits described above. Further still, exudate and/or other fluids produced by and/or adjacent the wound site can cause issues with wound oxygen treatment systems described above, including the introduction of blockages to the oxygen supply tubing/lines that prevent the provisioning of relatively high-concentration oxygen in the wound site enclosure and adjacent the wound site.

Accordingly, it would be desirable to provide an improved wound treatment system.

SUMMARY

According to one embodiment, a wound treatment system includes: a housing; a processor that is located in the housing; at least one sensor system that is coupled to the processor; a power delivery system that is located in the housing and that is coupled to the processor; an oxygen concentrator that is located in the housing and that is coupled to the power delivery system, wherein the oxygen concentrator includes an oxygen outlet that is coupled to a restricted airflow enclosure that is provided by a dressing and that is located adjacent a wound site; and a negative pressure system that is coupled to the processor, wherein the negative pressure system includes a negative pressure outlet that is coupled to the restricted airflow enclosure that is provided by the dressing and that is located adjacent the wound site; wherein the processor is configured to: receive first sensor information from the at least one sensor system; use the first sensor information to control the power provided from the power delivery system to the oxygen concentrator in order to control an oxygen flow created by the oxygen concentrator and provided through the oxygen outlet to the restricted airflow enclosure; receive second sensor information from at least one sensor system; and activate the negative pressure system to create a fluid flow from the restricted airflow enclosure and through the negative pressure outlet.

DETAILED DESCRIPTION

Figure 1:
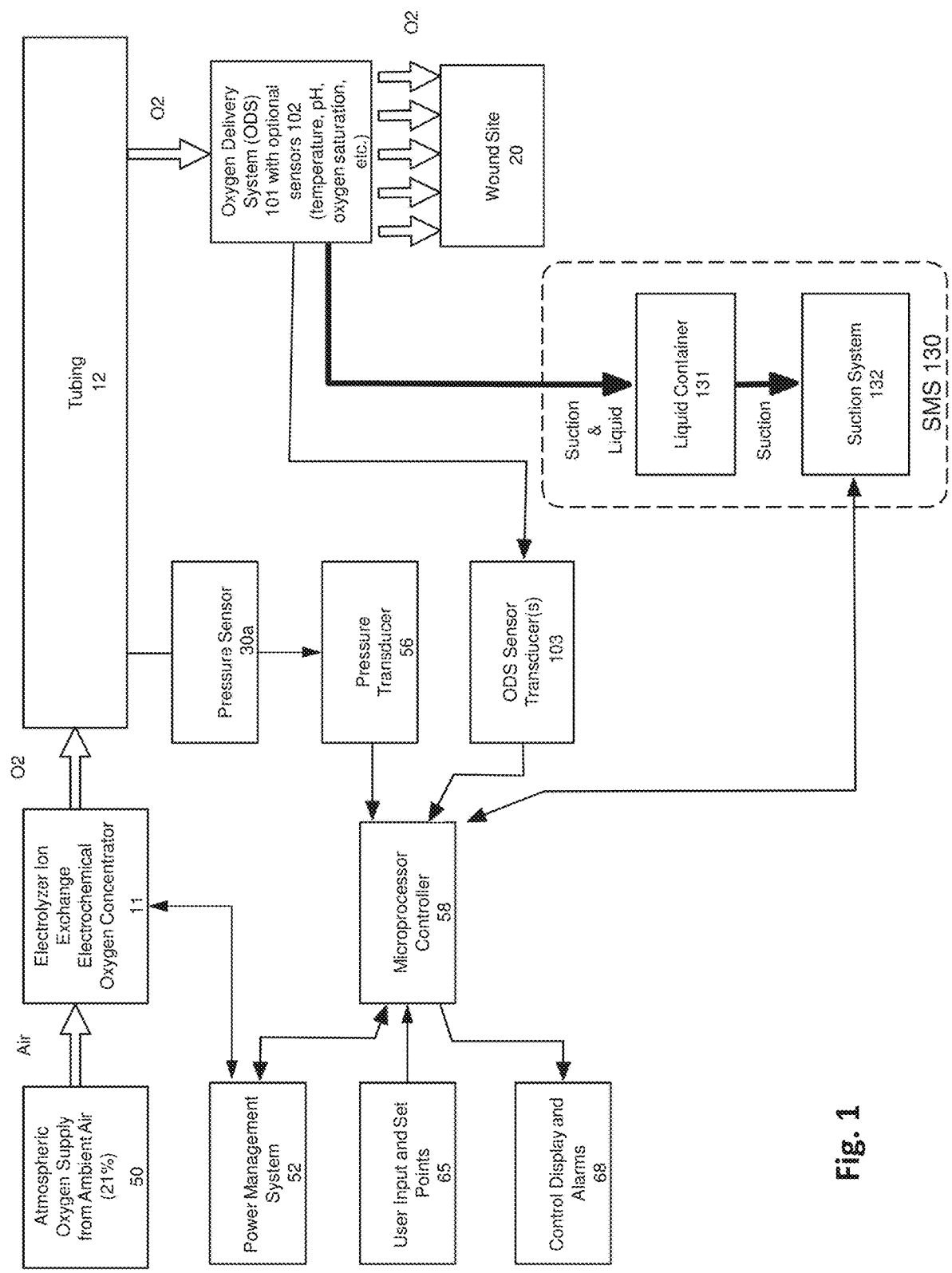
FIG. 1 is a schematic view illustrating an embodiment of a wound oxygen treatment system provided according to the teachings of the present disclosure.

Some embodiments of the present disclosure build off the teachings provided by at least some of the inventors of the present disclosure in the Incorporated References, the disclosures of which are incorporated by reference herein in their entirety.

U.S. Pat. No. 8,287,506 discloses a non-invasive tissue oxygenation system for accelerating the healing of damaged tissue and to promote tissue viability, comprising a lightweight portable electrochemical oxygen concentrator, a power management system, microprocessors, memory, a pressure sensing system, a temperature monitoring system, oxygen flow rate monitoring and control system, a display screen and key pad navigation controls as a means of providing continuous variably controlled low dosages of oxygen to a wound site and monitoring the healing process.

U.S. Pat. No. 10,226,610 discloses a wound treatment system including a housing, a processor located in the housing, a pressure monitoring system coupled to the processor to monitor pressure in a restricted airflow enclosure next to a wound site, a power delivery system located in the housing and coupled to the processor, an oxygen concentrator located in the housing and coupled to the power delivery system, and a plurality of oxygen outlets in the oxygen concentrator coupled to the restricted airflow enclosure, wherein the processor receives and uses pressure information from the pressure monitoring system to control power provided from the power delivery system to the oxygen concentrator, thereby controlling the oxygen flow provided through the oxygen concentrator outlets to the restricted airflow enclosure.

U.S. Patent Publication No. 2019/0001107 discloses a wound oxygen supply system that includes a chassis defining an oxygen outlet, an oxygen production subsystem in the chassis that is coupled to the oxygen outlet, and a control subsystem coupled to the oxygen production subsystem, wherein the control subsystem receives and uses humidity information from the oxygen production subsystem to control power provided to the production subsystem, thereby controlling the oxygen flow provided through the oxygen outlet to a restricted airflow enclosure next to a wound site.

The foregoing wound oxygen treatment systems may, for example, be configured according to the teachings of the present disclosure to intermittently remove excess fluids (e.g., wound exudate) from a wound dressing provided adjacent a wound using a negative pressure system, vacuum system, and/or suction management system (SMS). Such intermittent removal of exudate and/or other fluids from the wound dress operates to control wound exudate levels within the wound dressing and adjacent the wound site in order to protect the tissue from maceration, extend the life of the wound dressing (e.g., by increasing the time between wound dressing changes), and remove air from the restricted airflow enclosure provided between the wound dressing and the wound site so that higher oxygen concentrations may be achieved in a shorter timeframe relative to conventional systems (e.g., by removing nitrogen in the restricted airflow enclosure and decreasing the volume of air within the restricted airflow enclosure provided between the wound dressing and the wound site.) Excessive wound exudate may be produced in the early stages of Continuous Diffusion of Oxygen (CDO) therapy, with the levels of wound exudate varying over time and with the amount of oxygen being delivered. The removal of the wound exudate provides for better outcomes and user satisfaction, as well as reduced clinical management intervention (e.g., reducing overall cost to the health care system.)

The negative pressure, vacuum, and/or suction provided via the present disclosure may be achieved via mechanical, electromechanical, and/or other techniques that would be apparent to one of skill in the art in possession of the present disclosure. In some examples, the negative pressure, vacuum, and/or suction line may be separate from the oxygen supply line. In some examples, the negative pressure, vacuum, and/or suction system may be incorporated into the oxygen generation device, attached to it, or may be provided by a separate device. Furthermore, the negative pressure, vacuum, and/or suction system may include a container for the collection of wound exudate and/or other fluids.

In some embodiments, sensors in the oxygen generator and/or the wound dressing may be configured to indicate saturation and/or the presence of excess wound exudate in the wound dressing and/or adjacent the wound site, and may trigger the initiation of the removal of exudate via negative pressure, vacuum, and/or suction. Alternatively, the negative pressure, vacuum, and/or suction system may utilize timing algorithms based on feedback from the sensors in order to predict the presence of excess wound exudate and, in response, initiate the negative pressure, vacuum, and/or suction to remove the wound exudate and/or prevent the buildup of excess wound exudate levels.

In some embodiments, the negative pressure, vacuum, and/or suction system may provide for the removal of wound exudate for multiple wound oxygen treatment systems and/or multiple wound dressings, or may be provided with a single wound oxygen treatment system and a single wound dressing.

The wound oxygen treatment system may be capable of controlling the oxygen flow provided to the wound site based on the humidity of the air entering the electrolyzer provided in the oxygen concentrator. The use of air humidity to control the oxygen flow takes advantage of the fact that the flow of oxygen produced by the oxygen concentrator can be affected by the relative humidity of the air, with the electrolyzer becomes less efficient as the Nafion proton exchange membrane dries out. Above a threshold humidity, the electrolyzer operates at full efficiency and the flow of oxygen is linearly proportional to the current applied, while at humidity below the threshold, the efficiency of the electrolyzer becomes compromised and has a nonlinear response to current input. Hence, more current is required to maintain the desired flow of oxygen at relatively low humidity. In some embodiments, pressure may also be used in conjunction with humidity to modify the oxygen flow produced by the oxygen concentrator and prevent overpressurization of the restricted airflow enclosure provided by the wound dressing and located adjacent the wound site. The humidity sensor in the wound oxygen treatment system may be positioned so that it is exposed to ambient air before or after (or both before and after) humidity controls within the device (such as the use of a humidicant pack) are activated to humidify the incoming air.

The wound oxygen treatment system may include cell, power control, humidity and/or pressure sensors, and may use a smartphone or other computing device to monitor, control and provide power to wound oxygen treatment system. As such, the wound oxygen treatment system may include remote wound monitoring sensors, remote communication of data, and/or other high level functionality, but may also be minimized to be simply a local device (e.g., tethered to the smartphone discussed above) that provides oxygen and with no other inputs.

The negative pressure, vacuum, and/or suction system of the present disclosure may provide intermittent negative pressure, vacuum, and/or suction to optimize the oxygen concentration in the restricted airflow enclosure provided by the wound dressing adjacent the wound site, as well as removal of excess fluids and/or wound exudate from adjacent wound site. The negative pressure, vacuum, and/or suction may be attached to the wound dressing using a bifurcated tube that may include a microbore oxygen line and a medium bore vacuum line.

In some embodiments, the use of the wound oxygen treatment system initially includes applying an oxygen distribution wound dressing to the wound bed and adjacent the wound site, connecting the wound dressing to connective tubing that connects to the oxygen concentrator in the wound oxygen treatment system, and activating the wound oxygen treatment system. Activation of the wound oxygen treatment system may cause the generation of oxygen at a maximum flow rate, along with the generation of a negative pressure, vacuum, or suction that may be provided by a mechanical or a low power electrical vacuum pump. The negative pressure, vacuum, and/or suction may continue until a relative pressure of between −200 and −10, preferably between −100 and −70 mmHg, (e.g., max vacuum) is reached in the restricted airflow enclosure provided between the wound dressing and the wound site. Once a maximum negative pressure, vacuum, and/or suction is reached, the wound oxygen treatment system may produce oxygen at a maximum oxygen flow rate until a relative pressure in the restricted airflow enclosure provided by the wound dressing reaches 0 mm Hg. At this point, the oxygen concentrator may continue producing oxygen at a predetermined flow rate set point (e.g., a "steady state" flow rate), which may be selected by a physician.

At the steady state flow rate, the wound oxygen treatment system may continue producing oxygen at the oxygen flow rate set point, discussed above, and negative pressure, vacuum, and/or suction may be applied when the wound oxygen treatment system detects:

- A blockage alarm that indicates a blockage in an oxygen flow of oxygen from the oxygen concentrator to the wound site, which may be enable the activation of the negative pressure, vacuum, and/or suction to remove excess fluids and, in the process, relieve the blockage as well.
- Fluid saturation in the wound dressing that may be detected by a low-power, surface mount technology (SMT) fluid sensing membrane in the wound dressing (e.g., in the dressing layers) that may be used to measure saturation rates, and that may be used to signal the activation of negative pressure, vacuum, and/or suction via micro-wiring running thru the connection tubing between the dressing and the wound oxygen treatment system.
- A loss of dressing seal that the wound oxygen treatment system may monitor for via the monitoring of a pressure in the restricted airflow enclosure provided by the wound dressing adjacent the wound site, and that may provide for the initiation of negative pressure, vacuum, and/or suction to reseal the wound dressing when a minimum seal pressure is not maintained for a set period of time.
- Excessive time between negative pressure, vacuum, and/or suction applications. When the time between negative pressure, vacuum, and/or suction application events exceeds a maximum period of time (e.g., which may be based on a wound dressing type, a wound dressing size, a wound type, a wound size, and/or a combination of these (and other) variables).
- A dressing change, which may cause the wound oxygen treatment system to initiate a startup protocol to remove excess nitrogen from the restricted airflow enclosure provided by the wound dressing adjacent the wound site, and maximize oxygen concentration in that restricted airflow enclosure as quickly as possible.

In all of these cases, the negative pressure, vacuum, and/or suction may continue until a relative pressure of between −200 and −10, preferably between −100 and −70 mmHg, (e.g., "maximum vacuum") is achieved in the restricted airflow enclosure provided by the wound dressing adjacent the wound site. Once the maximum vacuum is achieved, the wound oxygen treatment system may produce oxygen at the maximum flow rate until the relative pressure within the dressing reaches 0 mm Hg. At this point, the oxygen concentrator may continue producing oxygen at a predetermined flow rate set point that may have been selected by a physician and that is referred to as steady state above.

Several embodiments of the above wound oxygen treatment system will now be described with reference to the figures, but one of skill in the art in possession of the present disclosure will recognize that a wide variety of modification to those embodiments will fall within the scope of the present disclosure as well. As such, different combinations of the different components and configurations of the wound oxygen supply systems discussed below, substitutions of different components in different wound oxygen supply systems, and/or any other modifications that would be apparent to one of skill in the art in possession of the present disclosure are envisioned as falling within the scope of the present disclosure.

With reference to FIG. 1, an embodiment of the wound oxygen treatment system of the present disclosure is illustrated. FIG. 1 illustrates how atmospheric oxygen supply from ambient air 50 with about 21% oxygen may enter an electrolyzer ion exchange electrochemical oxygen concentrator 11, which operates to concentrate the oxygen in the ambient air 50 to create an airflow that is high-concentration oxygen or O2, for example 99% pure oxygen. The high-concentration O2 is provided to oxygen delivery tubing 12, such that the high-concentration O2 is provided via an oxygen delivery system (ODS) 101 to damaged tissue or wound site 20.

ODS 101 may be comprised of one or more of the following: perforated tubing; porous membrane or tubing; a dressing with oxygen distribution; soft, flexible oxygen permeable tape or membrane; an oxygen-permeable bandage subsystem or section; or an oxygen delivery material or subsystem as described in the Incorporated References. In a basic form, ODS 101 may include no sensors for measuring its properties or characteristics. Alternatively, ODS 101 may incorporate one or more optional sensors or sensor interfaces 102 for measuring one or more properties, for example temperature sensors, pH sensors, oxygen saturation sensors, or other relevant sensors or sensor interfaces. If ODS 101 includes optional sensors 102, their output may be provided to one or more ODS sensor transducers 103.

A pressure sensor 30a or pressure sensor interface is coupled to the tubing 12, and provides information through a pressure transducer 56 to a microprocessor controller 58. The microprocessor controller 58 may also receive user input and set points 65, and information from any optional sensors 102 present in the ODS 101 and via optional ODS sensor transducers 103. The microprocessor controller 58 outputs control display and alarms 68, as well as controls a power management system 52 that provides power to the electrolyzer ion exchange electrochemical oxygen concentrator 11. As such, the information from the pressure sensor 30a may be utilized by the microprocessor controller 58 to control the power management system 52 to regulate power to the electrolyzer ion exchange electrochemical oxygen concentrator 11 in order to adjust the oxygen (O2) provided through the tubing 12 to the ODS 101 and the wound site 20. In addition, a suction management system (SMS) 130 is connected to the ODS 101, and includes a liquid reservoir or container 131 and a suction system 132 that can draw exudate and other fluids from the wound site 20 via the ODS 101, and store that exudate and other fluids in the liquid container 131. The suction management system 130 is also coupled to the microprocessor controller 58 to, for example, allow the microprocessor controller 58 to control the suction created by the suction and liquid system.

Figure 2:
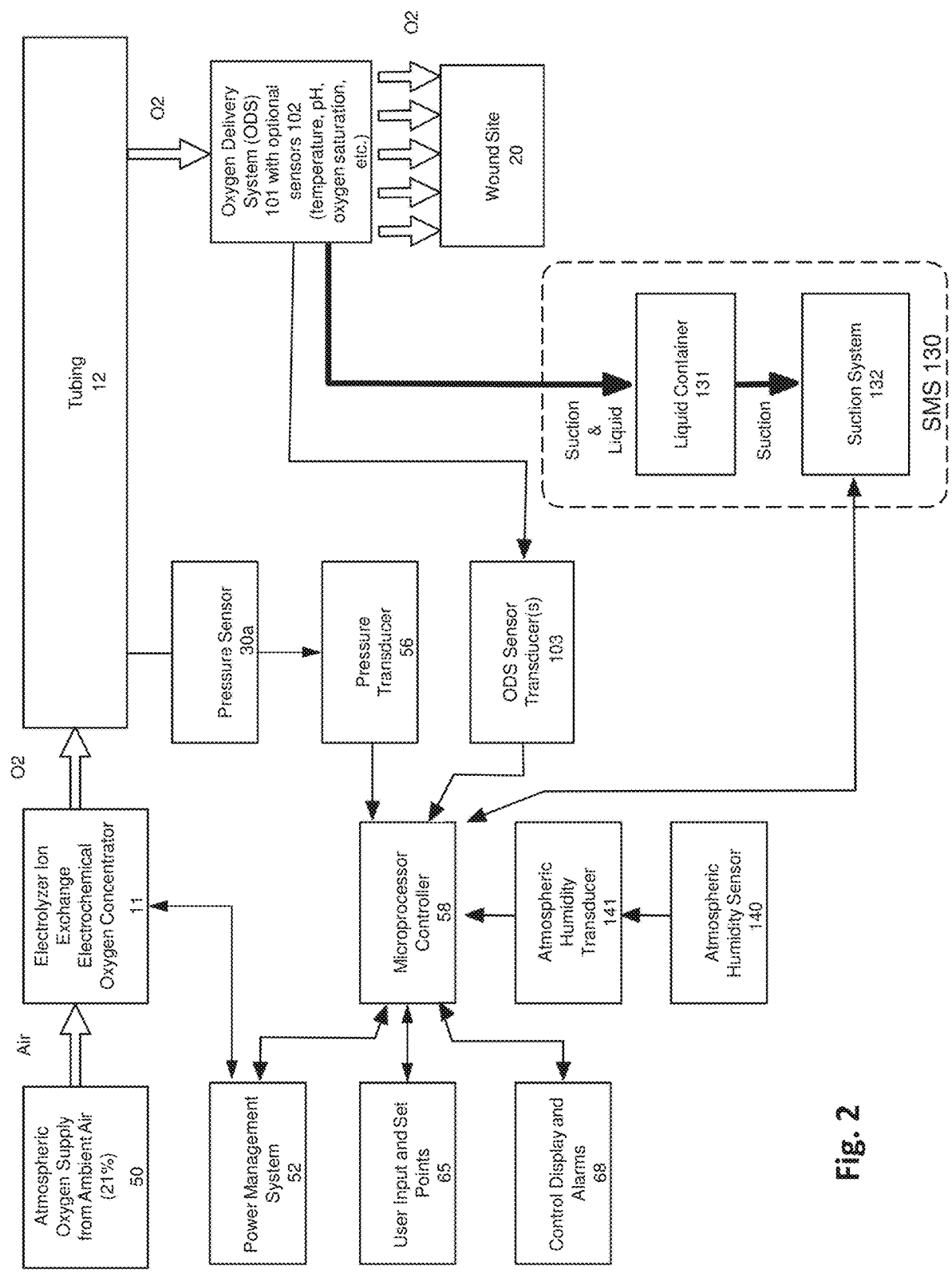
FIG. 2 is a schematic view illustrating an embodiment of a wound oxygen treatment system provided according to the teachings of the present disclosure.

With reference to FIG. 2, an embodiment of the wound oxygen treatment system of the present disclosure is illustrated that is substantially similar to the wound oxygen treatment system illustrated and discussed above with reference to FIG. 1, but with an atmospheric humidity sensor 140 providing information to the microprocessor controller 58 via an atmospheric humidity transducer 141. As such, the information from the atmospheric humidity sensor 140 may be utilized by the microprocessor controller 58 to control the power management system 52 to regulate power to the electrolyzer ion exchange electrochemical oxygen concentrator 11 in order to adjust the O2 provided through the tubing 12 to the ODS 101 and the wound site 20.

Figure 3:
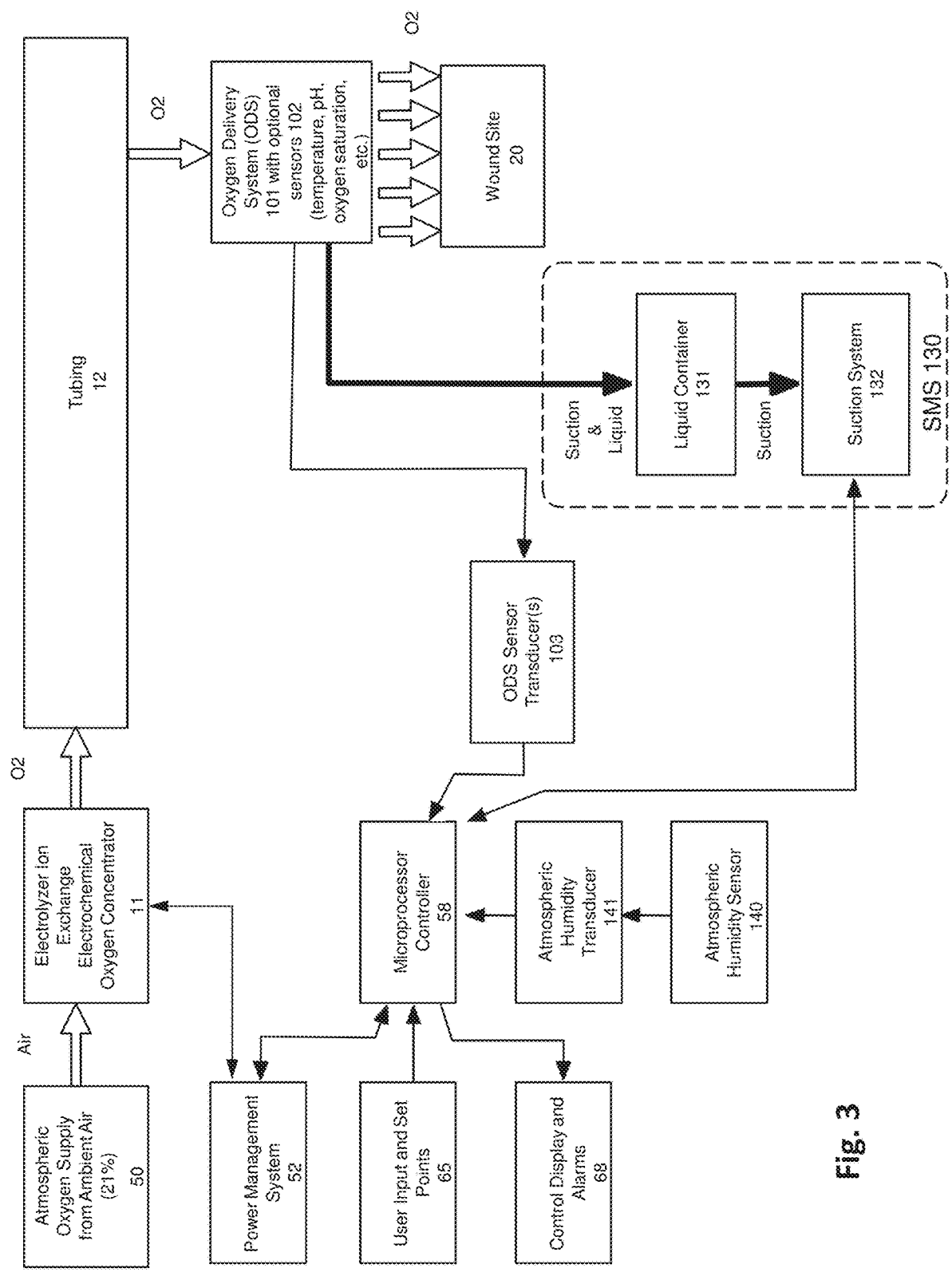
FIG. 3 is a schematic view illustrating an embodiment of a wound oxygen treatment system provided according to the teachings of the present disclosure.

With reference to FIG. 3, an embodiment of the wound oxygen treatment system of the present disclosure is illustrated that is substantially similar to the wound oxygen treatment system illustrated and discussed above with reference to FIG. 2, but with the removal of the pressure sensor 30a and pressure transducer 56. As such, the microprocessor controller 58 may need only the information from the atmospheric humidity sensor 140 to control the power management system 52 to regulate power to the electrolyzer ion exchange electrochemical oxygen concentrator 11 in order to adjust the O2 provided through the tubing 12 to the ODS 101 and the wound site 20.

Figure 4B:
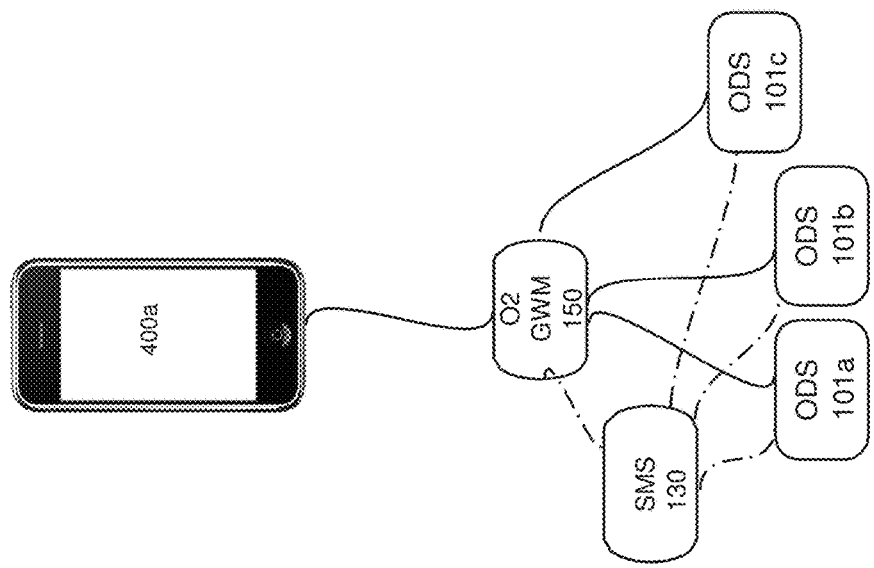
FIG. 4b is a schematic view illustrating an embodiment of a wound oxygen treatment system provided according to the teachings of the present disclosure.
Figure 4C:
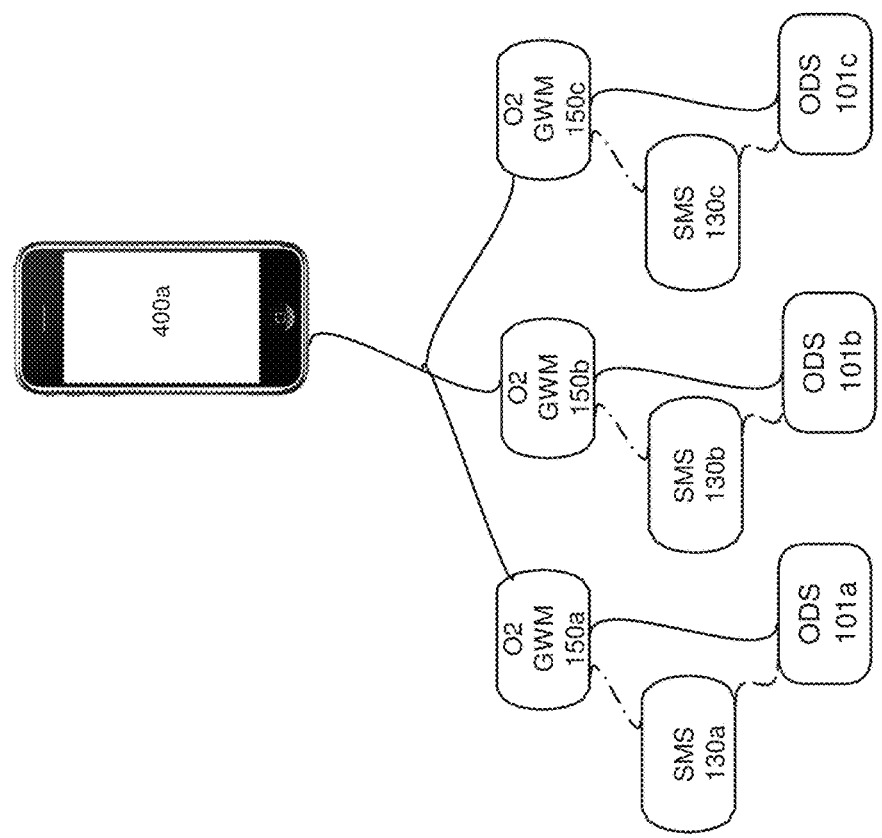
FIG. 4c is a schematic view illustrating an embodiment of a wound oxygen treatment system provided according to the teachings of the present disclosure.
Figure 4A:
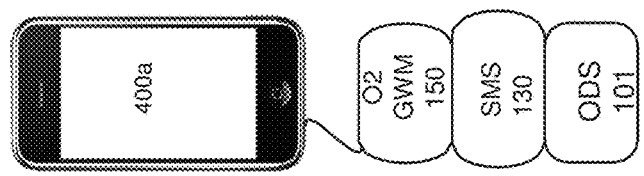
FIG. 4a is a schematic view illustrating an embodiment of a wound oxygen treatment system provided according to the teachings of the present disclosure.

With reference to FIGS. 4a, 4b, and 4c, different embodiments of the wound oxygen treatment system are illustrated that may be controlled by a smart phone or other mobile device 400a.

For example, in FIG. 4a, the suction management system 130 may be integrated with a single ODS 101 and may provide suction and liquid storage for that single ODS 101 that is controlled by a single smartphone/mobile device 400a via an oxygen generation and wound monitoring (O2 GWM) device 150.

In another example, illustrated in FIG. 4b, a single suction management system 130 may provide suction and liquid storage for multiple ODS 101 devices (ODS 101a, ODS 101b, and ODS 101c) that are controlled by a single smartphone/mobile device 400a via a single O2 GWM device 150.

In yet another example, illustrated in FIG. 4c, multiple suction management systems 130 (SMS 130a, SMS 130b, and SMS 130c) may provide suction and liquid storage for a single respective ODS 101 device (ODS 101a, ODS 101b, and ODS 101c) that are controlled by a single smartphone/mobile device 400a via multiple respective O2 GWM devices 150 (O2 GWM 150a, O2 GWM 150b, and O2 GWM 150c). Thus, the wound oxygen treatment system of FIG. 4c has one O2 GWM device 150 for each ODS 101 and suction management system 130 as illustrated.

An O2 GWM device 150 may be controlled wirelessly or tethered to the smartphone/mobile device 400a. In the case of a tethered connection, an O2 GWM 150 may by powered by the smartphone/mobile device 400a. In a similar manner, each suction management system 130 may be incorporated into a O2 GWM device 150, or it may be separate and controlled wirelessly or tethered to a O2 GWM device 150. For embodiments without an O2 GWM device 150, a suction management systems 130 may be controlled wirelessly or tethered to the microprocessor controller 48 or the smartphone/mobile device 400a.

Figure 5:
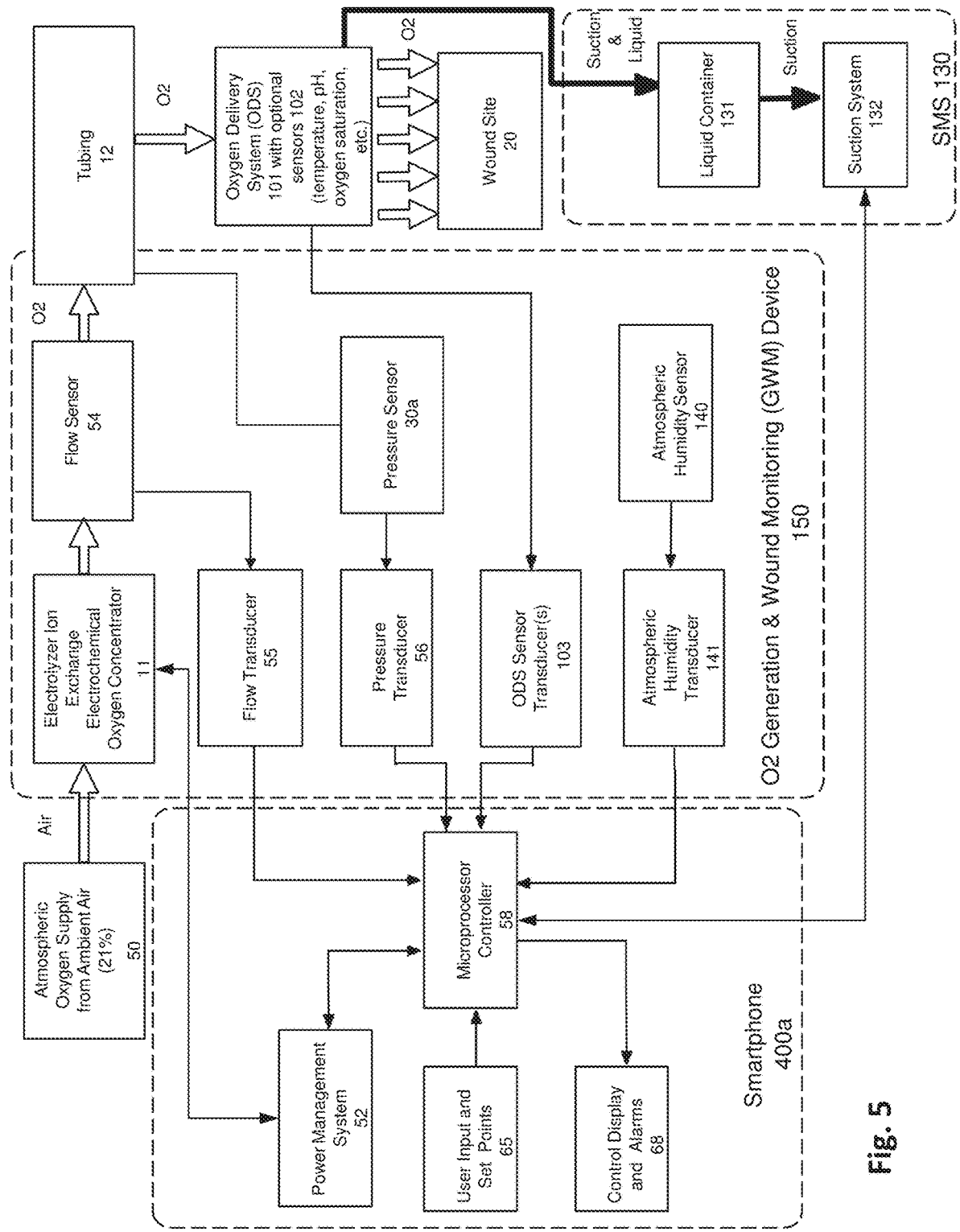
FIG. 5 is a schematic view illustrating an embodiment of a wound oxygen treatment system provided according to the teachings of the present disclosure.

With reference to FIG. 5, an embodiment of the wound oxygen treatment system of the present disclosure is illustrated that is substantially similar to the wound oxygen treatment system illustrated and discussed above with reference to FIG. 2, but with a flow sensor 54 providing information to the microprocessor controller 58 via a flow transducer 55 about an oxygen flow from the electrolyzer ion exchange electrochemical oxygen concentrator 11 to the tubing 12, and illustrating how different components may be provided by different devices (e.g., a smartphone 400a and an O2 GWM 150). As such, the information from the flow sensor 54 in the O2 GWM 150 may be utilized by the microprocessor controller 58 in the smartphone 400a to control the power management system 52 in the smartphone 400a to regulate power to the electrolyzer ion exchange electrochemical oxygen concentrator 11 in the O2 GWM 150 in order to adjust the oxygen (O2) provided through the tubing 12 to the ODS 101 and the wound site 20.

Figure 6:
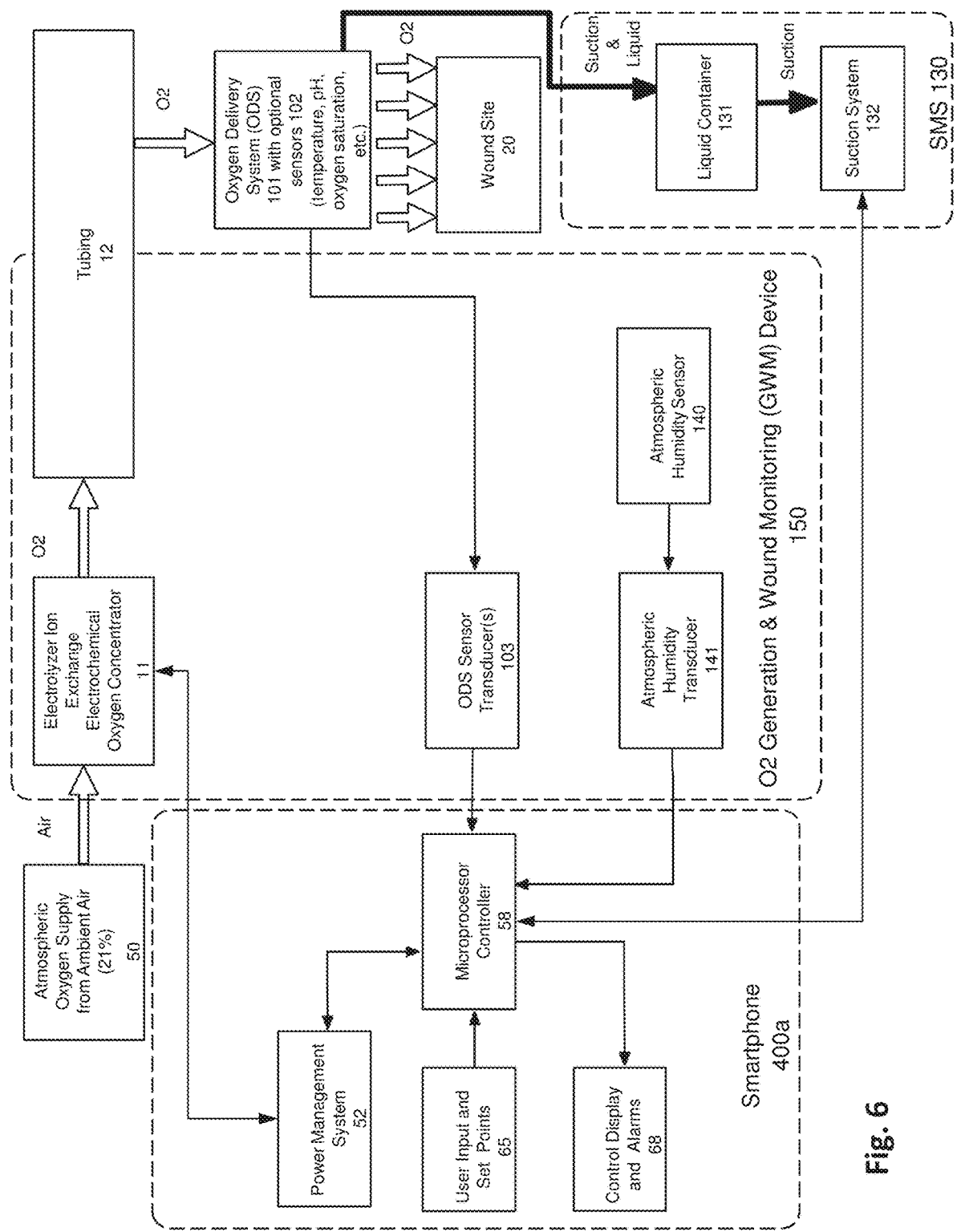
FIG. 6 is a schematic view illustrating an embodiment of a wound oxygen treatment system provided according to the teachings of the present disclosure.

With reference to FIG. 6, an embodiment of the wound oxygen treatment system of the present disclosure is illustrated that is substantially similar to the wound oxygen treatment system illustrated and discussed above with reference to FIG. 5, but with the removal of the pressure sensor 30a and pressure transducer 56, as well as the flow sensor 54 and the flow transducer 55. As such, the microprocessor controller 58 may need only the information from the atmospheric humidity sensor 140 to control the power management system 52 to regulate power to the electrolyzer ion exchange electrochemical oxygen concentrator 11 in order to adjust the oxygen (O2) Figs. through the tubing 12 to the ODS 101 and the wound site 20.

Although FIGS. 4a, 4b, 4c, 5, and 6 illustrate embodiments using a smartphone/mobile device 400a as a control device for the wound oxygen treatment system of the present disclosure, other computing devices such as, for example, tablet computing devices, laptop/notebook computing devices, desktop computing devices, smart watches, fitness trackers or other wrist mounted devices, and/or a variety of other computing devices may be provided as the control device while remaining within the scope of the present disclosure.

Similarly, while FIGS. 1-6 illustrate separate sensors and transducers for measuring pressure, humidity, flow, or other properties of the wound oxygen treatment system of the present disclosure and providing the measurement in a form usable by microprocessor controller 58, a sensor and its corresponding transducer may be combined into a single component or element that both measures a property of the system and converts the measurement into an electrical or other signal usable by microprocessor controller 58.

Although illustrative embodiments have been shown and described, a wide range of modification, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:
1. A wound treatment system, comprising:
a housing;
a processor that is located in the housing;
at least one sensor system that is coupled to the processor, wherein the at least one sensor system comprises a humidity sensor;
a power delivery system that is located in the housing and that is coupled to the processor;
an oxygen concentrator that is located in the housing and that is coupled to the power delivery system, wherein the oxygen concentrator includes an oxygen outlet that is coupled to a restricted airflow enclosure that is provided by a dressing and that is located adjacent a wound site; and
a negative pressure system that is coupled to the processor, wherein the negative pressure system includes a negative pressure outlet that is coupled to the restricted airflow enclosure that is provided by the dressing and that is located adjacent the wound site;
wherein the processor is configured to:
receive first sensor information from the at least one sensor system, wherein the first sensor information comprises atmospheric humidity information;
use the first sensor information comprising the atmospheric humidity information to control the power provided from the power delivery system to the oxygen concentrator in order to control an oxygen flow created by the oxygen concentrator and provided through the oxygen outlet to the restricted airflow enclosure;

receive second sensor information from the at least one sensor system; and activate the negative pressure system to create a fluid flow from the restricted airflow enclosure and through the negative pressure outlet.

2. The system of claim 1, wherein the second sensor information provides a blockage alarm that is indicative of a blockage in the coupling of the oxygen outlet to the restricted airflow enclosure.

3. The system of claim 2, wherein the blockage is caused by exudate produced at the wound site and that is located in the coupling of the oxygen outlet to the restricted airflow enclosure.

4. The system of claim 3, wherein activation of the negative pressure system to create the fluid flow from the restricted airflow enclosure and through the negative pressure outlet operates to remove the exudate that is located in the coupling of the oxygen outlet to the restricted airflow enclosure.

5. The system of claim 2, wherein the blockage is caused by an amount of oxygen that was created by the oxygen concentrator and provided through the oxygen outlet to the restricted airflow enclosure such that a pressure in the restricted airflow enclosure exceeds a maximum pressure.

6. The system of claim 1, wherein activation of the negative pressure system to create the fluid flow from the restricted airflow enclosure and through the negative pressure outlet operates to remove exudate produced at the wound site from the restricted airflow enclosure.

7. The system of claim 1, wherein activation of the negative pressure system to create the fluid flow from the restricted airflow enclosure and through the negative pressure outlet operates to achieve a dressing seal when a minimum seal pressure is not maintained for a set period of time.

8. The system of claim 1, wherein activation of the negative pressure system via a fluid saturation sensor creates the fluid flow from the restricted airflow enclosure and through the negative pressure outlet operates to remove exudate produced at the wound site from the restricted airflow enclosure.

9. The system of claim 1, wherein activation of the negative pressure system to create the fluid flow from the restricted airflow enclosure and through the negative pressure outlet operates to maximize oxygen concentration in that restricted airflow enclosure as quickly as possible.

* * * * *